United States Patent [19]

Augstein et al.

[11] Patent Number: 4,804,678
[45] Date of Patent: Feb. 14, 1989

[54] METHOD FOR TREATING ALLERGIC CONDITIONS

[75] Inventors: Joachim Augstein; Maqbool Ahmed, both of Loughborough, England

[73] Assignee: Fisons plc, Ipswich, England

[21] Appl. No.: 105,508

[22] Filed: Oct. 5, 1987

Related U.S. Application Data

[63] Continuation of Ser. No. 783,330, Oct. 3, 1985, abandoned, which is a continuation of Ser. No. 456,510, Jan. 7, 1983, abandoned.

[30] Foreign Application Priority Data

Jan. 22, 1982 [GB] United Kingdom ............... 8201883
Jul. 17, 1982 [GB] United Kingdom ............... 8220762

[51] Int. Cl.$^4$ ............................................. A61K 31/35
[52] U.S. Cl. ................................... 514/456; 514/826; 424/450
[58] Field of Search ............... 424/45, 450, DIG. 7; 514/460, 456; 428/402.2

[56] References Cited

U.S. PATENT DOCUMENTS 4,016,100  4/1977  Suzuki et al. .................. 428/402.2
4,186,183  1/1980  Steck et al. ........................ 424/38
4,217,344  8/1980  Vanlerberghe et al. ......... 424/38 X
4,235,871  11/1980 Papahodjopoulos et al. ... 428/402.2

FOREIGN PATENT DOCUMENTS

WO86/01714  3/1986  PCT Int'l Appl. ................ 424/450

OTHER PUBLICATIONS

The Merck Index, 9th Ed., p. 337.
Gregoriadis, *Drug Carriers in Biology and Medicine*, Academic Press, N.Y., 1979, Chapter 14.
Chem. Abs.: 98:221752x (1983).

*Primary Examiner*—Sam Rosen
*Attorney, Agent, or Firm*—Marshall, O'Toole, Gerstein, Murray & Bicknell

[57] ABSTRACT

There is described a pharmaceutical composition comprising liposomes and sodium cromoglycate.

There is also described an aqueous suspension comprising sodium cromoglycate partitioned between a free aqueous phase and a liposome phase.

There is further described a method for making the compositions, and their use in the treatment of allergic conditions, e.g., asthma.

10 Claims, No Drawings

METHOD FOR TREATING ALLERGIC CONDITIONS

This application is a continuation of application Ser. No. 783,330, filed Oct. 3, 1985, which is a continuation of application Ser. No. 456,510, filed Jan. 7, 1983, both now abandoned.

This invention relates to pharmaceutical compositions and more particularly it relates to the formulation of substances for inhalation.

Sodium cromoglycate has been known for a number of years for the treatment of allergic conditions, for example asthma, hay fever and vernal kerato conjunctivitis; however it suffers from the disadvantage that it is of relatively short duration of action.

According to the invention there is provided a pharmaceutical composition comprising liposomes and sodium cromoglycate.

By administering the liposomes of this invention directly into the site of the allergic condition, e.g. the lung, it is possible to effect an increased level of retention of sodium cromoglycate at the site, thereby obtaining increased duration of action.

The initial stages of the preparation of liposomes according to the present invention may conveniently follow procedures described in the art, i.e. the lipid starting materials being dissolved in a solvent, e.g. ethanol or chloroform, which is then evaporated. The resulting lipid layer is then dispersed in the selected aqueous medium containing an appropriate concentration of sodium cromoglycate. In contradistinction to the usual practice. however, it is preferred not to sonicate the liposomes thus produced, since this reduces their size. The liposomes produced by our procedure will usually be of a range of sizes. The liposomes of this invention preferably have a diameter of between 100nm. and 10 $\mu$m, more preferably they have a diameter of between 1 $\mu$m and 7 $\mu$m. It is known, for example, that liposomes having a diameter of up to 5000nm. may be readily phagocytosed. It is preferred that the liposomes are fractionated to remove substantially all those having a diameter less than 100nm., and preferably also those having a diameter less than 1 $\mu$m. Fractionation may conveniently be effected by column gel chromatography, for example using cross linked dextran or agarose, the size of the gel being selected according to the desired liposome size. Alternatively, the liposomes may be fractionated using ultracentrifugation, or by dialysis, e.g. using polycarbonate membrane filtration.

A wide variety of lipid materials may be used to form the liposomes including natural lecithins, e.g. those derived from egg and soya bean, and synthetic lecithins. Lipids which are non-immunogenic and bio-degradable are preferred. The properties of the lipid, for example its phase transition temperature, can have a marked effect on the retention and uptake of the liposomes in the target organ and for this reason the well defined synthetic lecithins are preferred to the natural lecithins. Examples of synthetic lecithins which may be used, together with their respective phase transition temperatures, are di-(tetradecanoyl)phosphatidylcholine (DTPC) (23° C.), di-(hexadecanoyl)phosphatidylcholine (DHPC) (41° C.) and di-(octandecanoyl)phosphatidylcholine (DOPC) (55° C.). We prefer to use di-(hexadecanoyl) phosphatidylcholine as the sole or major lecithin, optionally together with a minor proportion of the di-(octadecanoyl) or the di-(tetradecanoyl) compound. Other synthetic lecithins which may be used are unsaturated synthetic lecithins, for example di-(oleyl)phosphatidylcholine and di-(linoleyl)phosphatidylcholine. We prefer the synthetic lecithin, or the mixture of lipids, to have a phase transition temperature in the range 35°–45° C. In addition to the main liposome-forming lipid or lipids, which are usually phospholipids, other lipids (e.g. in a proportion of 5–40% w/w of the total lipids) may be included, for example cholesterol or cholesterol stearate, to modify the structure of the liposome membrane, rendering it more fluid or more rigid depending on the nature of the main liposome-forming lipid or lipids. An optional third component is a material which provides a negative charge, for example phosphatidic acid, dicetyl phosphate or beef brain ganglioside, or one which provides a positive charge for example stearylamine acetate or cetylpyridinium chloride. The charged component may be included in a proportion of 1–20% w/w of the total lipids.

A wide range of proportions of sodium cromoglycate to lipid during formation may be used depending on the lipid and the conditions used. However we have in general found that a range of one part by weight of sodium cromoglycate to from 0.01 to 100, preferably 0.05 to 20, most preferably 0.1 to 10 parts by weight of lipid is appropriate. We prefer to use as high a proportion of sodium cromoglycate as is practicable.

The concentration of sodium cromoglycate in the aqueous phase during liposome formation is preferably in the range 0.01 to 50mg/ml, and more preferably 0.1 to 20mg/ml, e.g. 10 or 20mg/ml.

We prefer the aqueous phase to contain less than 20 ppm of metal ions in group IIa, IB, IIB and IVb of the periodic table, and of the transition metals, in particular $Pb^{++}$, $Ca^{++}$, $Mg^{++}$, $Fe^{++}$ $Fe^{+++}$ and $Zn^{++}$ ions.

The aqueous phase may be made isotonic, using sodium chloride. In addition the aqueous phase may contain potassium chloride.

The aqueous phase may be adjusted to a pH of between 6 and 8, and preferably 6.5 to 7.5 by the addition of acid or base as appropriate, or by the addition of a suitable buffering agent, e.g. tris(hydroxymethyl)methanamine (Tris).

The concentration of lipid dispersed in the aqueous phase is preferably in the range 0.1 to 150mg/ml, more preferably 0.5 to 50mg/ml and most preferably 1 to 30mg/ml.

We prefer the liposome formulation to have a half life (efflux rate) at 37° C. of from about 12 to 48 and preferably 12 to 24 hours. Half lives may be measured using conventional techniques, e.g. by dilution methods. The half life of the formulation may be varied by varying the proportion of the various lipids used to make the liposome.

The compositions of the invention may be used for the treatment of asthma, by instilling a nebulised aqueous suspension of the sodium cromoglycate liposomes into the lungs. The compositions of the invention may be used as eye drops in the treatment of allergic eye conditions, e.g. vernal kerator conjunctivities, the occular symptoms of hay fever and/or marginal infiltration.

The compositions may also be used in the treatment of diseases of gastro-intestinal tract, e.g. ulcerative colitis, and food allergies, by oesophageal administration. Enemas incorporating the compositions may be used in the treatment of bowel diseases, particularly of allergic orgin. The compositions may also be used in the treatment of hay fever, by administration to the nose, e.g. as a nasal spray, and in the treatment of skin conditions, e.g. chronic dermatoses in mammals, notably man. Dermatoses which may be treated include those involving skin mast cells and/or antibody anitgen reactions and include eczemas, drug eruptions, psoriasis, dermatitis, herpetiformis pemphigus and chronic skin ulcers.

The compositions produced as described above are aqueous suspensions of liposomes in which sodium cromoglycate is partitioned between the free aqueous phase and the liposome phase.

We find that these aqueous formulations have useful and unexpected properties, in that the aqueous phase can provide an initial 'priming' dose of sodium cromoglycate, and the liposome phase can provide a maintenance dose of sodium cromoglycate. This has the effect of increasing the duration of action of sodium cromoglycate.

According to the invention, we therefore provide an aqueous suspension comprising sodium cromoglycate partitioned between a free aqueous phase and a liposome phase.

We prefer the total concentration of sodium cromoglycate in the aqueous suspension to be from 0.01 to 50mg/ml, and preferably 0.1 to 20mg/ml.

We prefer the percentage of sodium cromoglycte associated with the liposomes to be from 2 to 35% w/w, e.g from 4 to 20%. The percentage of sodium cromoglycate associated with the liposomes can be determined by conventional methods, e.g. centrifugation.

Alternatively, the aqueous suspension of sodium cromoglycate partitioned between an aqueous phase and a liposome phase, may be concentrated, e.g. by centrifugation, ultrafiltration or dialysis, to give a liposome gel. This gel may be used in several ways, e.g. it may be incorporated in an ointment base, resuspended in water or an isotomic, buffered saline solution, which may optionally contain sodium cromoglycate. Such formulations may be made up from the liposome gel, and suitable excipients immediately prior to use.

The dosage given will vary with the particular compositions used, the condition to be treated and its severity. We prefer to use an effective amount of sodium cromoglycate liposomes (e.g. for inhalation treatment of asthma, from 0.1 to 20mg) in the treatment of these conditions.

The invention is illustrated, but in no way limited by the following Examples.

General procedure for preparing sodium cromoglycate containing liposomes

The desired quantity (e.g. 20mg) of the appropriate phospholipid or mixture of phospholipids (e.g. egg lecithin, DTPC, DHPC or DOPC), together if desired with any other lipid soluble components (e.g. cholesterol, cholesterol stearate) is weighted into a round bottom flask. The lipid component is dissolved in a small quantity (ca 5ml) of a suitable solvent (e.g. ethanol), and evaporated to dryness under reduced pressure using a rotary film evaporator, to leave a thin film of phospholipid on the inner surface of the flask.

An aqueous solution of sodium cromoglycate of appropriate concentration (e.g. 1mg/ml) is prepared by dissolving a weighed amount of sodium cromoglycate in 20ml of an aqueous medium (e.g. 0.9% w/v saline solition, buffer solution, etc) and if desired the pH of the resulting solution can be adjusted to a selected value by the addition of acid or alkali. The aqueous solution of the sodium cromoglycate is warmed to a temperature 20° C. above the phase transition temperature of the lipid(s), added to the lipid film in the flask, and the flask gently shaken until all the lipid film is dispersed. The resulting suspension contains liposomes ranging from 200nm to 10um in size.

The suspension was allowed to equilibrate for 48 hours, at 37° C.

These suspensions contain sodium cromoglycate partitioning between the free aqueous phase and the liposome phase.

After 24 hours the suspension in most cases separates out to form a colloidal white precipitate, which is readily redispersed on shaking.

The following sodium cromoglycate liposomes compositions were prepared using the above general procedure:

| 1. | Egg lecithin | 20 mg |
| | Sodium cromoglycate | 200 mg |
| | Demineralised water | 20 ml |
| 2. | Egg lecithin | 20 mg |
| | Sodium cromoglycate | 20 mg |
| | Demineralised water | 20 ml |
| 3. | DTPC | 20 mg |
| | Sodium cromoglycate | 2 mg |
| | 0.9% w/v saline solution | 20 ml |
| 4. | DTPC | 20 mg |
| | Sodium cromoglycate | 20 mg |
| | 0.9% w/v saline solution | 20 ml |
| 5. | DTPC | 20 mg |
| | Sodium cromoglycate | 200 mg |
| | 0.9% w/v saline solution | 20 ml |
| 6. | DTPC | 200 mg |
| | Sodium cromoglycate | 200 mg |
| | 0.9% w/v saline solution | 20 ml |
| 7. | DTPC | 400 mg |
| | Sodium cromoglycate | 200 mg |
| | 0.9% w/v saline solution | 20 ml |
| 8. | DHPC | 200 mg |
| | Sodium cromoglycate | 200 mg |
| | 0.9% w/v saline solution | 20 ml |
| 9. | DOPC | 200 mg |
| | Sodium cromoglycate | 200 mg |
| | Demineralised water | 20 ml |
| 10. | DTPC | 133 mg |
| | Cholesteryl stearate | 67 mg |
| | Sodium cromoglycate | 200 mg |
| | Demineralised water | 20 ml |
| 11. | DHPC | 133 mg |
| | Cholesterol stearate | 67 mg |
| | Sodium cromoglycate | 200 mg |
| | Demineralised water | 20 ml |
| 12. | DHPC | 133 mg |
| | Cholesterol | 67 mg |
| | Sodium cromoglycate | 200 mg |
| | Demineralised water | 20 ml |
| 13. | DHPC | 20 mg |
| | Sodium cromoglycate | 200 mg |
| | 0.9% w/v saline solution | 20 ml |
| 14. | DHPC | 75 mg |
| | Sodium cromoglycate | 102.5 mg |
| | 150 mM potassium chloride 10 mM Tris buffer, pH 7.4 in water | 10 ml |
| 15. | DHPC | 70 mg |
| | DTPC | 30 mg |
| | Sodium cromoglycate | 100 mg |
| | 0.9 w/v saline solution | 10 ml |
| 16. | DHPC | 180 mg |
| | Sodium cromoglycate | 200 mg |
| | Cetylpyridinium chloride | 20 mg |
| | 0.9 w/v saline solution | 200 ml |

Determination of percentage sodium cromoglycate associated with liposomes

The equilibrated, sodium cromoglycate liposome dispersion is centrifuged at 70,000G for one hour. Aliquots of the supernatant are assayed in an ultraviolet spectrophotometer, at 326nm, to determine concentration of free sodium cromoglycate.

The percentage of sodium cromoglycate associated with the liposomes is determined from the relationship:

$$\text{percentage sodium cromoglycate (cromoglycate) associated with liposome} = \frac{[\text{Total cromoglycate}] - [\text{cromoglycate in supernatant}]}{[\text{Total cromoglycate}]} \times 100$$

The following percentage associations were determined:

| Example | |
|---|---|
| 5 | 4.5% w/w |
| 13 | 8.23% w/w |
| 14 | 14.00% w/w |

Rate of sodium cromoglycate release from liposomes, and liposome half-life

The rate of sodium cromoglycate release from the liposomes may be determined by centrifuging the sodium cromoglycate liposomes at 70,000G as above, discarding the supernatant and resuspending in isotomic saline, buffered at pH7.4. Aliquots of the resuspended liposomes, agitated at 37°C., were centrifuged at intervals, and the concentration of sodium cromoglycate in the supernatant determined by u.v. spectrophotometry. The release constant, k, of the liposome is determined by plotting ln [cromoglycate released] v time. The half-life of the liposome, $t_{\frac{1}{2}}$, is given by the relationship $t_{\frac{1}{2}} = (\ln 2)/k$.

Liposome half lives may also be determined using the dilution method described by M Ahmed et al, Biochemical Pharmacology, 29, 2361-2365, (1980).

Determination of flux and permeability coefficient

Preparation of Membranes

Albino hairless mice of either sex and aged 10 to 12 weeks were sacrificed by cervical dislocation and the dorsal skin removed with the minimum of handling. Any subcutaneous fat, visible as discrete globules, was removed. The skin samples were examined for any signs of damage before use. One skin sample was used per diffusion cell and was mounted, epidermal side up, over the opening in the upper section of the diffusion cell and was then secured with an 'O' ring. Excess skin was trimmed away before assembly of the cell.

Diffusion Cell Assembly

A small amount of silicone grease was applied to the 'O' ring of the upper section after securing the membrane. The upper section was then pushed firmly into the lower chamber until correctly positioned. The chamber was then filled with saline pre-equilibrated to 37°. The volume of each cell was adjusted individually to ensure that the skin membrane remained level. The fill volume was then marked on the sidearm.

Experimental Procedure

The set of eight diffusion cells were mounted on a carrier plate held in a thermostatically controlled water bath set at 37° C. and were allowed to equilibrate. Each cell was positioned over an underwater magnetic stirrer motor and the water level was adjusted to be approximately the same as the skin surfaces. This ensured that the temperature of the skin surface remained at 30°.

The vehicle to be studied was applied, either by delivery from a micropipette. The preparation was then evenly distributed over the exposed skin surface using a small glass rod. The weight of each aliquot applied was determined by accurately weighing at least 10 samples delivered by the micropipette or syringe.

Following application of the vehicle the magnetic stirrers were switched on and at appropriate time intervals 1.0ml samples of the receptor fluid were removed via the side arms and immediately replaced with fresh saline pre-equilibrated to 37°. The samples were then deep frozen until analysed for the drug by High Performance Liquid Chromatography (HPLC).

At least three replicate diffusion cells were used for each formulation studied.

Data Handling

Assuming that only passive diffusion occurs during the transport of the drug across the skin, the rate of penetration can be given by Fick's law.

$$J = P \Delta C$$

Where
 J is the flux, the amount of drug diffusing per unit area per unit time,
 P is the permeability coefficient
 $\Delta C$ is the concentration difference across the stratum corneum.

We claim:

1. A method of treatment of an allergic condition which comprises administration by inhalation of an aqueous suspension in a free aqueous phase of liposomes containing sodium cromoglycate said suspension comprising an effective amount of sodium cromoglycate partitioned between said free aqueous phase and said liposomes to a patient suffering from said condition.

2. A method in accordance with claim 1 wherein said liposomes have diameters between 100 nm and 100 μm.

3. A method in accordance with claim 1 wherein said liposomes comprise one or more natural or synthetic lecithins.

4. A method in accordance with claim 3 wherein said composition further includes a component having a negative or positive charge.

5. A method in accordance with claim 3 wherein said lecithins have a phase transition temperature in the range of 35°–45° C.

6. A method in accordance with claim 5 wherein said liposomes contain at least one additional component selected from the group consisting of cholesterol and cholesterol stearate.

7. A method in accordance with claim 1 wherein said liposomes comprise a lipid and sodium cromoglycate in a ratio by weight of sodium cromoglycate to lipid of 0.01 to 100.

8. A method in accordance with claim 1 wherein the total concentration of sodium cromoglycate in said suspension is from 0.01 to 50 mg/ml.

9. A method in accordance with claim 1 wherein the concentration of sodium cromoglycate in said suspension is 2–35% by weight.

10. A method in accordance with claim 1 wherein said suspension comprises 0.1 to 20 mg/ml of sodium cromoglycate and said liposome phase comprises at least one of the lecithins di-(tetradecanoyl)phosphatidylcholine, di((hexadecanoyl)phosphatidylcholine and di-(octadecanoyl) phosphatidylcholine, the concentration of lecithins dispersed in the aqueous phase is from 1 to 30 mg/ml and the percentage of sodium cromoglycate associated with the liposomes is from 2 to 35% w/w.

* * * * *